(12) United States Patent
Adelman et al.

(10) Patent No.: US 9,864,834 B2
(45) Date of Patent: Jan. 9, 2018

(54) HIGH-RESOLUTION MELT CURVE CLASSIFICATION USING NEURAL NETWORKS

(71) Applicant: SRC, Inc., North Syracuse, NY (US)

(72) Inventors: Jonathan David Adelman, Mexico, NY (US); William Ryon McKay, East Syracuse, NY (US); Jacquelyn Lillis, Cicero, NY (US); Katherine Lawson, Syracuse, NY (US)

(73) Assignee: Syracuse University, Syracuse, NY (US)

( * ) Notice: Subject to any disclaimer, the term of this patent is extended or adjusted under 35 U.S.C. 154(b) by 687 days.

(21) Appl. No.: 13/833,446

(22) Filed: Mar. 15, 2013

(65) Prior Publication Data

US 2014/0278126 A1    Sep. 18, 2014

(51) Int. Cl.
*G06F 19/00* (2011.01)
*G06F 19/24* (2011.01)

(52) U.S. Cl.
CPC .................................. *G06F 19/24* (2013.01)

(58) Field of Classification Search
CPC ... A61B 5/7221; A61B 5/7235; A61B 5/7239; G06F 17/10; G06F 17/11; G06F 17/18; G06F 19/3412; G06F 19/707; G06F 17/13; G06F 17/3028; G06F 17/30371; G06F 17/30421; G06F 17/30548; G06F 19/24

See application file for complete search history.

(56) References Cited

U.S. PATENT DOCUMENTS

| | | | |
|---|---|---|---|
| 7,035,740 B2 | 4/2006 | Kermani | |
| 7,582,429 B2 | 10/2009 | Wittwer | |
| 7,892,745 B2 | 2/2011 | Wohlgemuth | |
| 8,271,205 B2 * | 9/2012 | Reja | G06F 19/24 |
| | | | 700/1 |
| 2002/0097910 A1 * | 7/2002 | Guha | G06K 9/222 |
| | | | 382/187 |
| 2003/0068825 A1 | 4/2003 | Washburn | |
| 2004/0260476 A1 * | 12/2004 | Borgos | G01V 1/301 |
| | | | 702/14 |
| 2009/0204353 A1 | 8/2009 | Cheng | |
| 2011/0045479 A1 | 2/2011 | Tobler | |

FOREIGN PATENT DOCUMENTS

CN        101955989        1/2011

OTHER PUBLICATIONS

Zhang et al. Weights and Structure Determination of Feed-Forward Two-Input Neural Network Activated by Chebyshev Polynomials of Class 2. 2012 24th Chinese Control and Decision Conference (CCDC) [Online] 2012, pp. 1100-1105.

* cited by examiner

*Primary Examiner* — Mary K Zeman
(74) *Attorney, Agent, or Firm* — Bond Schoeneck & King, PLLC; Frederick Price; George McGuire

(57) ABSTRACT

The present invention relates to a method and system for classifying high-resolution melt ("HRM") curves, and, more specifically, to a method and system for classifying HRM curves by genotype where the curves are represented by a mathematical function with varying coefficient values.

5 Claims, 3 Drawing Sheets

HIGH-RESOLUTION MELT CURVE CLASSIFICATION USING NEURAL NETWORKS

BACKGROUND OF THE INVENTION

1. Field of the Invention

Figure 1:
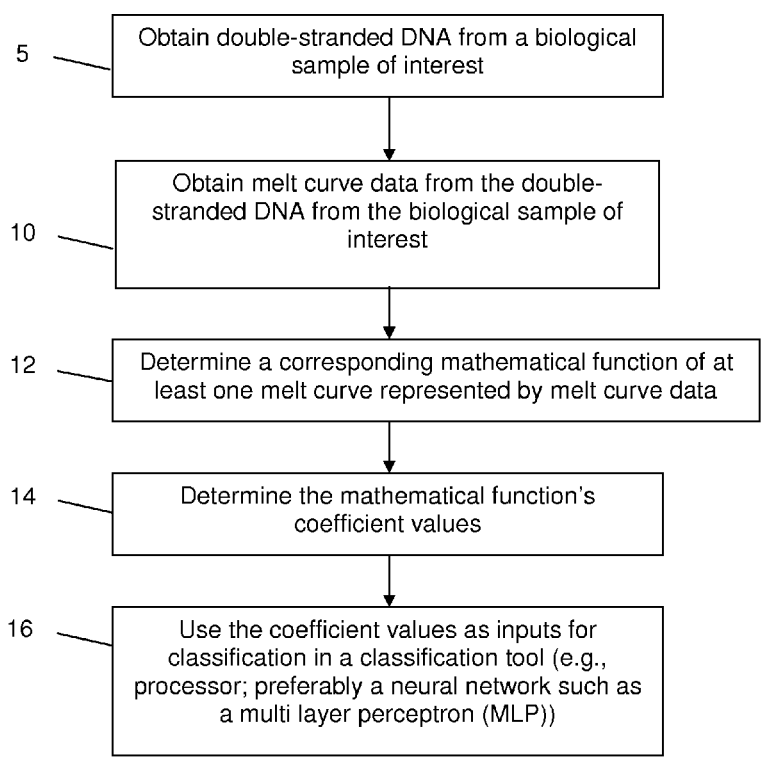

The present invention relates to a method and system for classifying high-resolution melt ("HRM") curves, and, more specifically, to a method and system for classifying HRM curves by genotype where the curves are represented by a mathematical function with varying coefficient values.

2. Description of the Related Art

High-Resolution Melt ("HRM") is a molecular biology tool. This tool can be used to detect a variety of differences (e.g., mutations) in samples of double stranded DNA, which is based on the detected melting temperature/behavior of the double stranded DNA sequence(s) at issue. HRM is usually performed post PCR amplification, which is performed to obtain a sufficient number of copies of the DNA sequence(s) of interest.

Most current approaches to high-resolution melt classification involve software that (1) normalizes a series of HRM curves, and then (2) uses a subtraction plot comparing a given melt curve with a pre-defined control. Such a method is unable to probabilistically assess classification results; curves are assigned only a "yes" or "no" value for membership to a given genotype class. Such a method is also unable to evaluate and classify HRM curves across multiple runs of the thermal cycler (or other platform used to generate such curves), or across multiple platforms.

BRIEF SUMMARY OF THE INVENTION

It is therefore a principal object and advantage of the present invention to provide a method and system for classifying HRM curves by genotype where the curves are represented by a mathematical function with varying coefficient values.

Another object and advantage of the present invention is to provide a method and system for classifying HRM curves by genotype even when curves are generated over the course of several distinct melts or on more than one different thermal cycler platforms. Stated differently, an object and advantage of the present invention is to provide a method and system for classifying HRM curves by genotype that produces at least as accurate results than has been seen by any prior art method or system and is not limited to analysis of data generated from a single usage of a thermal cycler.

In accordance with the foregoing objects and advantages, a method is provided comprising one or more of the following: a method for classifying high resolution melt ("HRM") curve data by genotype, the method comprising one or more of the following steps: obtaining melt curve data from double-stranded DNA from an obtained biological sample of interest; determining, by a processor, a corresponding mathematical function of at least one melt curve represented by melt curve data; determining, by the processor, the mathematical function's coefficient values using the coefficient values as inputs for classification in a classification tool, wherein the classification tool is configured to classify the melt curve data as either a known genotype or an unknown genotype based on the inputted coefficient values.

In accordance with another embodiment of the present invention, a non-transitory medium is provided comprising one or more of the following: a non-transitory computer-readable storage medium containing program code comprising: program code for obtaining melt curve data from a double-stranded DNA from an obtained biological sample of interest; program code for determining a corresponding mathematical function of at least one melt curve represented by melt curve data; program code for determining the mathematical function's coefficient values; program code for using the coefficient values as inputs for classification in a classification tool, wherein the classification tool is configured to classify the melt curve data as either a known genotype or an unknown genotype based on the inputted coefficient values.

The details of one or more embodiments are described below and in the accompanying drawings. Other objects and advantages of the present invention will in part be obvious, and in part appear hereinafter.

BRIEF DESCRIPTION OF THE SEVERAL VIEWS OF THE DRAWING(S)

Figure 2:
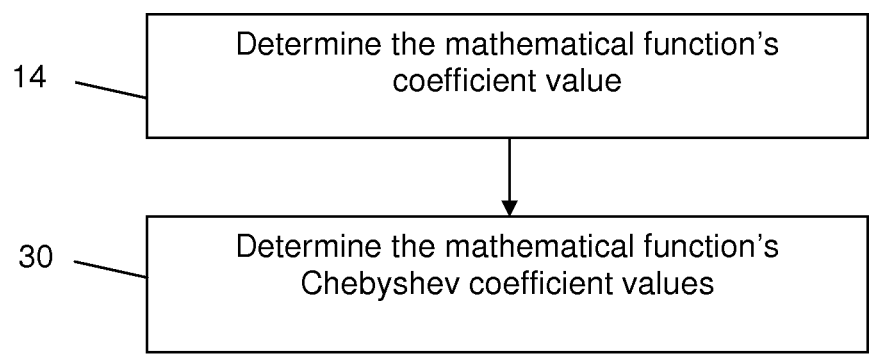
Figure 3:
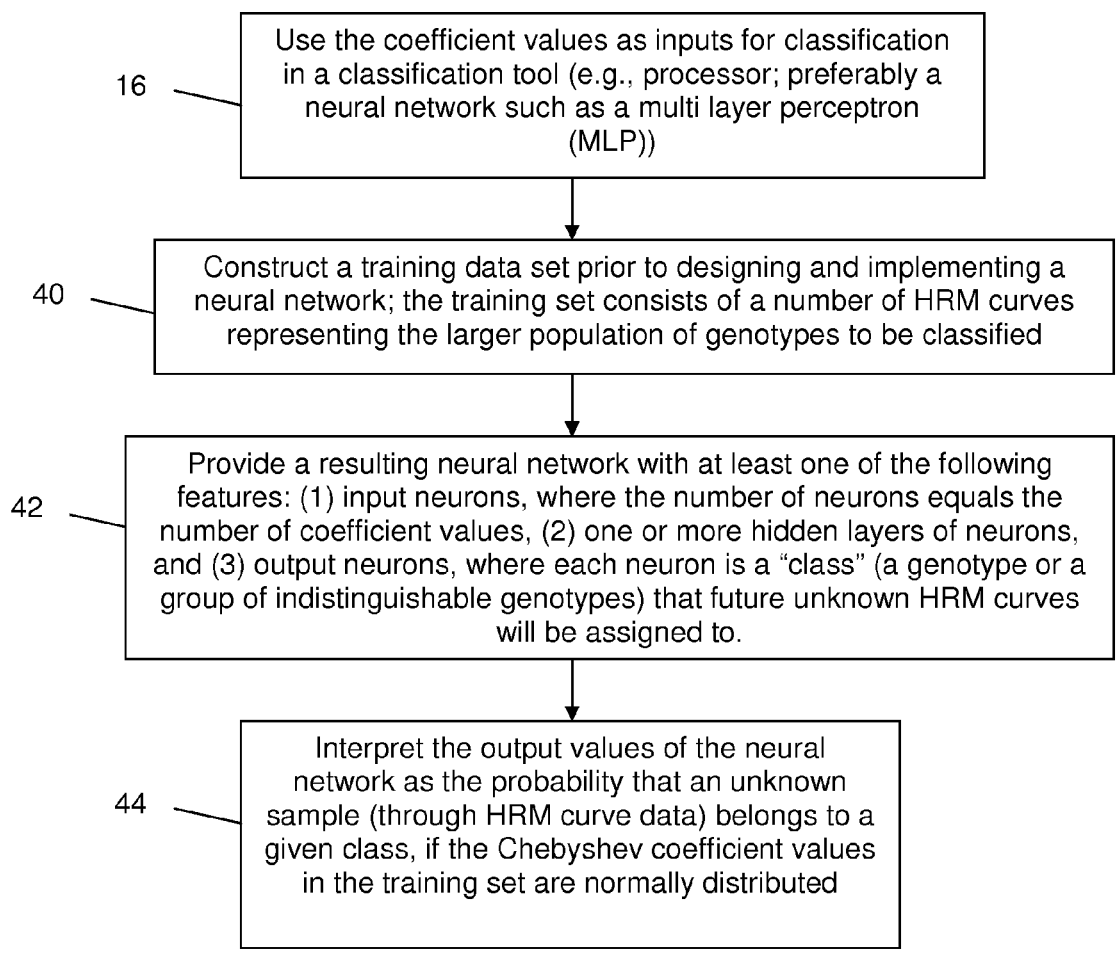

The present invention will be more fully understood and appreciated by reading the following Detailed Description in conjunction with the accompanying drawings, in which:

FIG. 1 a schematic representation of an embodiment of the method according to the present invention;

FIG. 2 is a schematic representation of an embodiment of the method according to the present invention; and FIG. 3 is a schematic representation of an embodiment of the method according to the present invention.

DETAILED DESCRIPTION OF THE INVENTION

Advantages of the invention are illustrated by the Examples set forth herein. However, the particular conditions and details are to be interpreted to apply broadly in the art and should not be construed to unduly restrict or limit the invention in any way.

As discussed herein, it was discovered that because a HRM curve can be conceived as a mathematical function, curve-fitting can be used to assign function coefficient values to each curve and allow subsequent robust classification. The use of DNA was investigated as a means of identifying persons, species, or genotypes of interest to the defense and intelligence communities, for example. HRM "curves" (in reality these are discrete time/fluorescence data, but will be referred to as curves hereafter) of double-stranded DNA from biological samples can be relied on as a powerful, cost effective means of genotyping samples of interest. Because each melt curve corresponds to a genotype, a major component of this effort can be the classification of melt curves into distinct genotypes.

EXAMPLE

This Example describes the development of a methodology for the classification of high-resolution melt curves by genotype. This methodology involves an initial compression of information in the melt curve's derivative melt profile through the means of a function such as a Chebyshev polynomial expansion, followed by the evaluation of that function's coefficients by a locus-specific artificial neural network. This approach—robust curve compression followed by machine learning classification—allows the user to probabilistically evaluate samples across runs, to classify samples as either known genotypes or unknowns, and to potentially classify complex DNA mixtures.

An HRM curve may initially seem like a misnomer; the corresponding temperature and fluorescence data are measured discretely and plotted as x-y coordinates. Nonetheless there are many points (usually >100 after a melt is finished), and when these discrete data are reported in the literature they are typically replaced with a corresponding curve which reflects the fact that the process being measured is actually continuous. The majority of approaches for classifying these curves involve the measuring of the area between the sample of interest and a known, classified curve from the same run.

An alternate approach—the approach described herein and part of an embodiment of the present invention—is to determine a mathematical function that corresponds to the shape of an HRM curve and then classify by analyzing the function itself. This approach is a direct response to a principle common to many different classification methodologies, referred to as the "curse of dimensionality". Many classification tools involve the analysis of high-dimension spaces; in such a scenario, as the number of inputs to the classification tool increases linearly then the tool's required complexity increases exponentially. An enormous amount of observations are therefore required to correctly classify a high-dimension dataset, and limiting the number of inputs becomes vital. By finding a mathematical function that strongly correlates with a given array of x-y data, the curve can in essence be "collapsed," and the curve's information can be represented with high fidelity by using only a handful of numbers. These numbers—the function's coefficients—can then become the inputs to a classification tool.

As set forth below, two examples of functions that can be used to compress a melt curve while retaining its information are discussed. That is a key aspect of this particular part of the invention—curve compression to avoid the "curse of dimensionality" while maintaining the curve's information. The particular function is chosen is less important, and these functions that are discussed are some of many plausible functions that can be used for the same purposes (e.g., a function that can strongly correlate to a melt curve).

The initial example HRM curves of interest were relatively simple, with no "bumps", only one melt temperature (TM), and a clear shape that could be attributed to a low-order sigmoid function. A variant of the Gompertz function (Equation 1) was initially chosen to represent these melt curves. The highest asymptote of this sigmoid function is approached much more slowly than is the lowest asymptote, lending Gompertz functions an asymmetric quality that mirrors HRM curves.

The equation is as follows:

$$f(x) = a * e^{\wedge}(-e^{\wedge}(-(x-x_0)/b)) \quad (1)$$

where f(x) is the normalized fluorescence, a is the upper asymptote, b is a curvature parameter, x is the temperature, x0 is the temperature at the curve's inflection point (i.e. the TM), and e is Euler's number.

Many of the HRM curves of interest are more complex, however, and the need to accurately model bumps, shoulders, and other such curve characteristics led to an evaluation of Chebyshev polynomial expansions (Equation 2). The equation is as follows:

$$T_0(x) = 1$$

$$T_1(x) = x$$

$$T_{n+1}(x) = 2 \times T_n(x) - T_{n-1}(x) \quad (2)$$

where T0(x) is the Chebyshev polynomial at order 0, T1(x) is the Chebyshev polynomial at order 1, etc. The function is thereby recursively defined, as it requires the two previous order expansions in order to determine the current-order expansion. Chebyshev polynomial expansions and their coefficients are used to compress a complex HRM curve's information (specifically, the information in the negative of the curve's first derivative, referred to in the industry as a Derivative Melt Profile), and the coefficients are then used as inputs for classification.

Classification itself occurs via an artificial neural network (hereafter "neural network" or "NN"). A multi-layer perceptron (MLP) is a common type of neural network often used in classification, and there already exists a great deal of literature on its back propagation learning algorithm. However, the construction and use of the neural network described herein is unique.

Because this is a supervised learning approach, the user must construct a training data set prior to designing and implementing a neural network; the training set consists of a number of HRM curves representing the larger population of genotypes to be classified. The user may choose to optimize network parameters such as learning rate or momentum. MLP construction then follows using back propagation, and the resulting neural network will have the following features: (1) input neurons, where the number of neurons equals the number of coefficients, (2) one or more hidden layers of neurons, and (3) output neurons, where each neuron is a "class" (a genotype or a group of indistinguishable genotypes) that future unknown HRM curves will be assigned to. If the coefficients in the training set are normally distributed, an output value of the neural network can be interpreted as the probability that an unknown sample belongs to a given class.

Referring now to the drawings, wherein like reference numerals refer to like parts throughout, there is seen in FIG. 1 a schematic representation of an embodiment of the method according to the present invention. As shown in FIG. 1, pursuant to the discussion set forth herein and above, as an initial step 5, double-stranded DNA from a biological sample of interest is obtained. In step 10, melt curve data are obtained from the double-stranded DNA from the biological sample of interest. In step 12, the corresponding mathematical function of at least one melt curve represented by melt curve data are determined. In step 14, the mathematical function's coefficient values are determined. In step 16, the coefficient values are used as inputs for classification in a classification tool (e.g., processor; preferably a neural network such as a multi layer perceptron (MLP)).

FIG. 2 is a schematic representation of an embodiment of the method according to the present invention. As shown in FIG. 2, step 14 can further include step 30, which is simply a specific example, or one possible way of specifically carrying out, step 14. In step 30, the mathematical function's Chebyshev coefficient values are determined. Again, a Chebyshev polynomial expansion is one possible function that can be used. Other functions, such as a Gompertz function, may be more appropriate in a particular case.

FIG. 3 is a schematic representation of an embodiment of the method according to the present invention. As shown in FIG. 3, step 16 can further include steps 16, 40, 42, and 44. In step 40, a training data set prior to designing and implementing a neural network; the training set consists of a number of HRM curves representing the larger population of genotypes to be classified is constructed. In step 42, a resulting neural network with at least one of the following features is provided: (1) input neurons, where the number of neurons equals the number of coefficients, (2) one or more hidden layers of neurons, and (3) output neurons, where each neuron is a "class" (a genotype or a group of indistinguishable genotypes) that future unknown HRM curves will be assigned to. In step 44, the output values output values of the neural network are interpreted as the probability that an unknown sample belongs to a given class, if the coefficients in the training set are normally distributed.

As will be appreciated by one skilled in the art, aspects of the present invention including the embodiments of the method described herein may be embodied/implemented as a computer system, method or computer program product. The computer program product can have a computer processor or neural network, for example, that carries out the instructions of a computer program. Accordingly, aspects of the present invention may take the form of an entirely hardware embodiment, an entirely software embodiment or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction performance system, apparatus, or device.

The program code may perform entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

As discussed above, an embodiment of the present invention may be used to classify HRM curves by genotype. Specific applications include but are not limited to (1) cost-effective genotyping of humans of interest to criminal, intelligence, and/or defense analysts, (2) cost-effective genotyping of cultivars for a plant or animal of interest to breeders, and (3) cost-effective genotyping of plant or animal species (or genotypes within the species) of interest to the intelligence community (e.g. different genotypes of illicit drugs grown from plant products can have distinct geospatial origins).

Although the present invention has been described in connection with a preferred embodiment, it should be understood that modifications, alterations, and additions can be made to the invention without departing from the scope of the invention as defined by the claims.

What is claimed is:

1. A method for classifying high resolution melt ("HRM") curve data by genotype, the method comprising:
    obtaining melt curve data from double-stranded DNA from an obtained biological sample of interest by heating the obtained biological sample of interest and measuring a resulting change in fluorescence as a function of a temperature of the obtained biological sample of interest;
    fitting, by a processor, a corresponding mathematical function to at least one melt curve represented by melt curve data, wherein the step of fitting fits the data with a Chebyshev polynomial expansion;
    determining, by the processor, the mathematical function's coefficient values;
    inputting the coefficient values into a classification tool for classification comprising a neural network, wherein the neural network comprises at least one of the following neuron types:
        input neurons, where the number of neurons equals the number of coefficient values;
        one or more hidden layers of neurons; and
        plurality of output neurons, wherein each of said output neurons represents a class comprising a genotype or a group of indistinguishable genotypes that unknown HRM curve data will be assigned to; and
    classifying the melt curve data by the neural network as either a known genotype or an unknown genotype based on the inputted coefficient values.

2. The method of claim 1, wherein the step of fitting, by the processor, the mathematical function's coefficient values further comprises determining the mathematical function's Chebyshev coefficient values.

3. The method of claim 2, wherein the step of using a Chebyshev polynomial expansion is pursuant to the following equation:

$$T_0(x)=1$$

$$T_1(x)=x$$

$$T_{n+1}(x)=2\times T_n(x)-T_{n-1}(x)$$

where T0(x) is the Chebyshev polynomial at order 0, and T1(x) is the Chebyshev polynomial at order 1.

4. The method of claim 1, wherein the step of using the coefficient values as an input for classification in a classification tool further comprises the step of constructing a training data set prior to designing and implementing the classification tool, wherein the training data set comprises HRM curve data representing a population of genotypes to be classified.

5. The method of claim 1, further comprising the step of interpreting output values of the neural network as the probability that an unknown HRM curve data belongs to a given class, if the coefficient values in the training set are normally distributed.

* * * * *